United States Patent [19]

Toraya et al.

[11] Patent Number: 5,405,839
[45] Date of Patent: Apr. 11, 1995

[54] VITAMIN B$_{12}$ DERIVATIVE, PREPARATION PROCESS THEREOF, AND USE THEREOF

[75] Inventors: Tetsuo Toraya; Atsuhiko Ishida, both of Okayama; Yasuhide Uejima, Hino; Katsuhiko Fujii, Hachioji, all of Japan

[73] Assignee: Teijin Limited, Osaka, Japan

[21] Appl. No.: 104,606

[22] Filed: Aug. 11, 1993

Related U.S. Application Data

[63] Continuation of Ser. No. 601,778, filed as Pct/JP90/00253, Feb. 28, 1990, abandoned.

[30] Foreign Application Priority Data

Feb. 28, 1989 [JP]  Japan .................................. 1-45172

[51] Int. Cl.$^6$ ........................ A61K 31/68; C07H 23/00
[52] U.S. Cl. ...................................... 514/52; 536/26.4; 536/26.41
[58] Field of Search .......................... 536/2, 6.41, 26.4; 514/52

[56] References Cited

FOREIGN PATENT DOCUMENTS

| | | | |
|---|---|---|---|
| 0069450 | 1/1983 | European Pat. Off. ...... | C07H 23/00 |
| 2752756 | 6/1978 | Germany ..................... | C07H 23/00 |
| 0012909 | 12/1978 | Germany . | |

OTHER PUBLICATIONS

"Inorganic Chemistry of Vitamin B$_{12}$", by J. M. Pratt, Academic Press, 1972 pp. 156–159.

G. L. Matevosyan et al., "Preparation of Phosphorylated Benzimidazoles", Journal of General Chemistry of the USSR, vol. 52, No. 7, part 1, Jul. 1982 pp. 1275–1286.

*Primary Examiner*—John W. Rollins
*Assistant Examiner*—James O. Wilson
*Attorney, Agent, or Firm*—Sughrue, Mion, Zinn, Macpeak & Seas

[57] ABSTRACT

Vitamin B$_{12}$ compounds, salts and pharmaceutical compositions containing said compounds represented by formula (I):

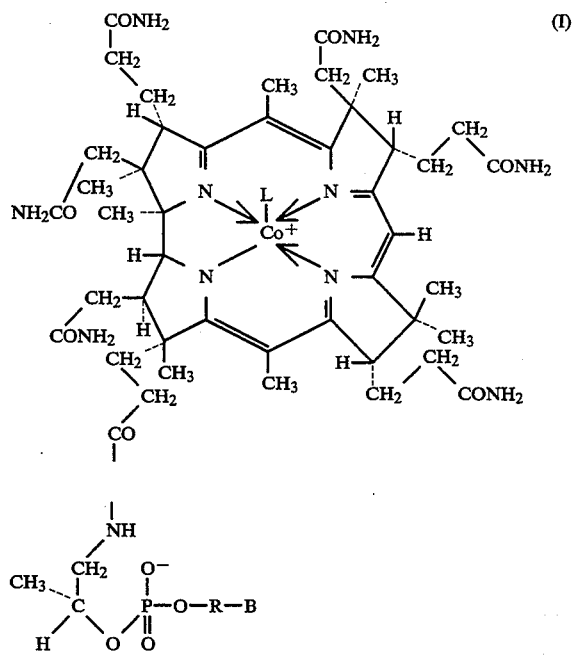

wherein L, a ligand to the cobalt of the corrin ring, is selected from the group consisting of a cyano or adenosyl group, B is an imidazole group or a 5,6-dimethylbenzimidazole group, and R is a straight alkylene group having 1 to 8 carbon atoms, are disclosed. Methods for preparing compounds of Formula (I) as well as methods for using the compounds in in vitro assays, in cell growth studies and in in vivo studies using transplanted murine tumor cells are disclosed.

2 Claims, 1 Drawing Sheet

Fig.1

VITAMIN $B_{12}$ DERIVATIVE, PREPARATION PROCESS THEREOF, AND USE THEREOF

CROSS REFERENCES TO RELATED APPLICATIONS

The instant application, which is 08/104,606, filed Aug. 11, 1993, is a continuation of U.S. patent application Ser. No. 07/601,778, filed as Pct/JP90/00253, Feb. 28, 1990, now abandoned.

TECHNICAL FIELD

The present invention relates to a novel vitamin $B_{12}$ derivative and a salt thereof, a process for producing the same, and a use thereof. More specifically, it relates to a vitamin $B_{12}$ derivative and a salt thereof represented by the formula (I):

wherein L represents a ligand to the cobalt of the corrin ring, B a base having a heterocyclic structure, and R a substituted or nonsubstituted hydrocarbon group, a process for preparing the same, a vitamin $B_{12}$ antagonistic agent, and a cell growth inhibiting or interfering agent containing the same as the active ingredient.

BACKGROUND ART

Vitamin $B_{12}$ is an essential nutrient factor required for human and animals in a minute amount. In mammals, it is contained relatively abundantly in the liver. Neither animals nor plants can biosynthesize this vitamin, which can be produced only by microorganisms. As a disease due to a lack of vitamin $B_{12}$, pernicious anemia is particularly representative thereof, and megaloblastic hemopoiesis, methylmalonic acid uria, homocystinuria, and neuropathy, etc., are caused thereby. When absorbed into the body, vitamin $B_{12}$ is converted to a metabolically active vitamin $B_{12}$ coenzyme (adenosylcobalamin) and methylcobalamin; the former functioning as a coenzyme in an enzymatic reaction accompanied by a movement of hydrogen, such as methylmalonyl CoA mutase, and the latter functioning as a coenzyme in an enzymatic reaction accompanied by a movement of a methyl group, such as methionine synthetase. Particularly, methylcobalamin functions in a $C_1$ metabolism involving a folic acid coenzyme, thereby participating indirectly in a biosynthesis of thymidylic acid and playing an important role in cell growth. Accordingly, a compound exhibiting an antagonistic activity against the vitamin $B_{12}$ group, i.e., a vitamin $B_{12}$ antagonist, may be considered to suppress or inhibit cell growth by interfering with the DNA synthesis, and to be effective as an antitumor agent (anticancer agent) against tumor cells (cancer cells). Also, the vitamin $B_{12}$ group is important for the growth of microorganisms, and the vitamin $B_{12}$ antagonist is considered to have an activity as an antimicrobial agent. Conversely, the vitamin $B_{12}$ antagonist may be considered to be applied for screening a microorganism mutant strain having a high vitamin $B_{12}$ productivity, with a resistance thereto as the index.

In the prior art, various vitamin $B_{12}$ derivatives have been synthesized and, for example, it is known that the vitamin $B_{12}$ derivatives synthesized chemically or microbiologically from cobyric acid and having the isopropanolamine moiety ($-NHCH_2CH(CH_3)O-$) converted to, for example, $-NHCH(CH_3)CH_2O-$, $-NHCH_2CH_2CH_2O-$, $-NHC(CH_3)_2CH_2O-$, $-NHCH_2CH(C_6H_5)O-$ or $-NHCH_2CH(CH_2F)O-$, exhibit an antagonistic activity against *Escherichia coli* 113-3 and *Lactobacillus leichmannii* (Friedrich, Vitamin $B_{12}$ und verwandte Corrinoid (Georg Thieme Verlag, Stuttgart), p. 289–308, 1975). Also, cobalt-free corrinoid isolated from a microorganism, or a different kind of metal corrinoid in which, for example, rhodium, copper, and zinc, are introduced into a cobalt-free corrinoid, is known to exhibit a similar antagonistic activity against the above-mentioned microorganisms (Friedrich, Vitamin $B_{12}$ und verwandte Corrinoid (Georg Thieme Verlag, Stuttgart), p. 289–308, 1975, and Copenhagen, $B_{12}$ (John Wiley & Sons, New York), vol. II, p. 105–149, 1982).

Nevertheless, the preparation of cobyric acid is complicated and it is difficult to obtain same in a large amount, and when a microorganism is used, a problem arises in practical application due to the isolation thereof.

Also, vitamin $B_{12}$ derivatives having a bromine or nitro group introduced into the C-10 position of the corrin ring, and vitamin $B_{12}$ derivatives in which the surrounding side chains of the corrin ring are derivatized to, for example, carboxyl group, ethylamide, anilide, and hydrazide, have been chemically synthesized (Friedrich, Vitamin $B_{12}$ und verwandte Corrinoid (Georg Thieme Verlag, Stuttgart), p. 289–308, 1975), but these derivatives are still unsatisfactory due to a low antagonistic activity thereof.

Accordingly, there is a need for a vitamin $B_{12}$ antagonist having an excellent antagonistic activity, and which can be supplied in a large amount.

DISCLOSURE OF THE INVENTION

Accordingly, an object of the present invention is to provide a novel vitamin $B_{12}$ antagonist having an excellent antagonistic activity, and which can be supplied in a large amount.

Another object of the present invention is to provide a process for preparing a vitamin $B_{12}$ derivative having an excellent $B_{12}$-antagonistic activity, and which can be supplied in a large amount.

A further object of the present invention is to provide a novel vitamin $B_{12}$ antagonistic agent.

A still further object of the present invention is to provide a novel cell growth inhibiting or interfering agent.

A still further object of the present invention is to provide a novel antitumor agent.

A still further object of the present invention is to provide a method of screening a microorganism mutant strain of high vitamin $B_{12}$ productivity.

Other objects and advantages of the present invention will be apparent from the following descriptions.

In accordance with the present invention, there is provided a vitamin $B_{12}$ derivative and a salt thereof represented by the formula (I):

wherein L represents a ligand to the cobalt of the corrin ring, B a base having a heterocyclic structure, and R a substituted or nonsubstituted hydrocarbon group, a vitamin $B_{12}$ antagonistic agent, a cell growth inhibiting or interfering agent, and an antitumor agent containing the same as the active ingredient.

BRIEF DESCRIPTION OF THE DRAWINGS

In the Figure, A represents the control, B the results when methotrexate (MTX) (200 nM) was added, C when MTX (200 nM) and the vitamin $B_{12}$ derivative obtained in Example 2 (50 nM) were added, and D and E when MTX (200 nM) and the vitamin $B_{12}$ derivatives obtained in Example 5 were added at concentrations of 50 nM and 5000 nM, respectively.

BEST MODE OF CARRYING OUT THE INVENTION

The present inventors made intensive studies of the problems of the prior art as described above, and found that the vitamin $B_{12}$ derivatives of the formula (I) obtained by a modification of the ribose moiety of the nucleotide portion of the vitamin $B_{12}$ group can be supplied in a large amount, and have a very good vitamin $B_{12}$ antagonist activity.

In the vitamin $B_{12}$ derivative represented by the formula (I), L represents a ligand to the cobalt of the corrin ring. Examples of the ligand represented by L include a cyano group, substituted or nonsubstituted adenosyl group or adeninylalkyl group (alkyl group is a straight or branched alkyl group having 1 to 8 carbon atoms), hydroxyl group, water molecule, or a straight or branched alkyl group having 1 to 8 carbon atoms, and further, L can be represented by two of these groups, which may be the same or different. Alkyl groups having 1 to 8 carbon atoms, are preferably a methyl group, ethyl group, and propyl group. The ligand L is generally coordinated above the corrin ring, but can be on either side of the corrin ring, or can exist on both sides thereof.

In the formula (I), R is a substituted or nonsubstituted hydrocarbon group, and is exemplified by an alkylene group having 1 to 8 carbon atoms, which is substituted by an aromatic group or a halogen atom or is nonsubstituted, or a cyclic hydrocarbon group. An alkylene group having 1 to 8 carbon atoms is preferred.

In the formula (I), B represents a base having a heterocyclic structure, as exemplified by a substituted or nonsubstituted imidazole group, pyridine group, or derivatives thereof. As such derivatives, a benzimidazole group having a benzene ring fused to imidazole group, or a 5,6-dimethylbenzimidazole group, which is a derivative thereof, are included. This base B is coordinated generally below the cobalt of the corrin ring, but in the present invention, the case wherein it is not coordinated is included.

Also, the present invention provides a process for preparing the vitamin $B_{12}$ derivative represented by the formula (I).

More specifically, (1) cyanoaquacobinamide or dicyanocobinamide is allowed to react with a phosphoric acid ester derivative or a salt thereof represented by the following formula (II):

wherein B and R are the same as defined in the above formula (I), to prepare a corresponding compound of the formula (I) wherein L is a cyano group.

The reaction between the compound represented by the formula (II) and cyanoaquacobinamide or dicyanocobinamide can be carried out by using, for example, a condensing agent, preferably dicyclohexylcarbodiimide, in an organic solvent, preferably a mixed solution of pyridine and N,N-dimethylformamide. The reaction temperature must not be higher than the boiling temperature of the solvent employed, and is, for example, preferably around room temperature. Cyanoaquacobinamide is prepared easily from vitamin $B_{12}$ (cyanocobalamin) or dicyanocobinamide. The compound represented by the formula (I), wherein L is a cyano group obtained as a result of a reaction, can be purified by extraction, column chromatography, and (or) high performance liquid chromatography.

Alternatively, (2) the compound represented by the formula (I) wherein L is a cyano group can be reduced and then subjected to a) reoxidation, or b) alkylation followed by photolysis to be converted into a compound represented by the formula (I) wherein L is a hydroxyl group or water molecule, or (3) the compound represented by the formula (I) wherein L is a cyano group, hydroxyl group or water molecule can be reduced with, for example, sodium borohydride, zinc and ammonium chloride, zinc and acetic acid, or divalent chromium, and then reacted with, for example, a halogenated alkane (the alkyl moiety is a straight or branched alkyl group having 1 to 8 carbon atoms, preferably a methyl group, ethyl group, or propyl group), or a halogenated or tosylated substituted or nonsubstituted adenosine or adeninylalkane (the alkyl moiety is a straight or branched alkyl group having 1 to 8 carbon atoms), for example, preferably 5′-halo-5′-deoxyadenosine, to prepare a corresponding compound represented by the formula (I). These compounds can be obtained as purified products by, for example, extraction or column chromatography. The obtained compound represented by the formula (I) can be also reacted with, for example, sulfuric acid to form a salt.

Further, the present invention concerns a phosphoric acid ester derivative represented by the formula (II) and a salt thereof, and a method of preparing same. These phosphoric acid ester derivatives and salts thereof are useful intermediates for the preparation of the vitamin $B_{12}$ derivatives of the present invention represented by the formula (I), and can be obtained by the methods described below.

Namely, the phosphoric acid ester derivative represented by the formula (II) and a salt thereof is prepared by reacting a free base B′ having a heterocyclic structure with a compound represented by the following formula (III):

(XXX)

wherein X represents a leaving group, and R is the same as defined in the above formula (I) to obtain a compound represented by the following formula (IV):

(XV)

wherein B and R are the same as defined in the above formula (I), and subsequently, phosphorylating this compound, preferably by using a 2-cyanoethylphosphoric acid pyridinium salt.

The free base B′ having a heterocyclic structure can be, for example, a substituted or nonsubstituted imidazole, pyridine, or a derivative thereof, and examples of the imidazole derivatives include benzimidazole or 5,6-dimethylbenzimidazole. These compounds B′ are commercially available, or can be prepared by known methods.

In the compound represented by the formula (III), X represents a leaving group which is, for example, a halogen atom, preferably a chlorine atom. The compound represented by the formula (III) is commercially available or can be obtained by known methods.

The reaction between the free base B′ having a heterocyclic structure and the compound represented by the formula (III) may be carried out in the presence of a base, preferably sodium hydride or potassium carbonate, at a reaction temperature of preferably around room temperature, or the reaction may be carried out by heating under reflux. This reaction is carried out in an organic solvent, preferably N,N-dimethylformamide, or dioxane. The compound represented by the formula (IV), which is the reaction product, can be used as crude product for the subsequent reactions, but preferably is separated and purified from the reaction mixture by known methods such as washing, extraction or column chromatography, before use.

A phosphorylation of the compound represented by the formula (IV) is practiced in the presence of, for example, a condensing agent, preferably 2-cyanoethylphosphoric acid pyridinium salt, followed by the reaction with lithium hydroxide. As the condensing agent, dicyclohexylcarbodiimide is preferable, and the reaction is carried out in an organic solvent, preferably pyridine, at a reaction temperature not higher than the boiling point of the solvent employed, preferably around room temperature. The 2-cyanoethylphosphoric acid pyridinium salt can be easily prepared from 2-cyanoethylphosphoric acid barium salt, according to the method of Tener (J. Am. Chem. Soc., vol. 83, p. 159-168, 1961). The compound represented by the formula (II), which is the reaction product, can be used as the crude product for the intermediate for the preparation of the vitamin $B_{12}$ derivative represented by the formula (I), or if desired, can be separated and purified from the reaction mixture by known methods such as filtration, extraction or column chromatography, or if preferable, in the form of a salt such as lithium, sodium, potassium, barium or pyridine, by known methods.

The vitamin $B_{12}$ derivatives represented by the formula (I) have highly beneficial pharmacological properties. Namely, these compounds have vitamin $B_{12}$ antagonist activities, can be used as vitamin $B_{12}$ antagonistic agents, and exhibit better antagonistic activities than known vitamin $B_{12}$ antagonists. Further, since the vitamin $B_{12}$ derivative represented by the formula (I) makes use of cyanoaquacobinamide or dicyanocobinamide as the starting material, according to the preparation method as described above, it can be also supplied more simply and in a larger amount than known vitamin $B_{12}$ antagonists. Also, the vitamin $B_{12}$ derivatives represented by the formula (I) of the present invention can be used as a cell growth inhibiting or interfering agent containing at least one thereof as the antimicrobial agent when the cell is a microorganism, or as the antitumor agent (anticancer agent) when the cell is an animal cell, particularly a tumor cell (cancer cell). When used as such a cell growth inhibiting or interfering agent, the compound can be formulated into a pharmaceutical preparation comprising at least one active ingredient of the vitamin $B_{12}$ derivatives represented by the formula (I), and a pharmaceutically acceptable carrier and (or) necessary additives.

The vitamin $B_{12}$ derivatives represented by the formula (I) of the present invention act antagonistically against the vitamin $B_{12}$ group, and therefore, growth of microorganisms producing a high quantity of vitamin $B_{12}$ will be suppressed weakly by the vitamin $B_{12}$ derivatives represented by the formula (I), or will not be suppressed at all. Therefore, a subject matter of the present invention is also the use of the vitamin $B_{12}$ derivative of the present invention, for screening a microorganism mutant strain of high vitamin $B_{12}$ productivity.

As described above, the vitamin $B_{12}$ derivative of the present invention has a vitamin $B_{12}$ antagonistic activity, and is very useful for the study of a vitamin $B_{12}$ group during an enzymatic reaction, for example, a coenzyme function thereof. Further, the vitamin $B_{12}$ derivative of the present invention exhibits a very good antagonistic activity, and the cell inhibiting or interfering agent containing such a vitamin $B_{12}$ derivative as the active ingredient is useful as, for example, an antimicrobial agent or antitumor agent (anticancer agent). Also, the vitamin $B_{12}$ derivative of the present invention can be used for screening a microorganism mutant of high vitamin $B_{12}$ productivity. Further, the vitamin $B_{12}$ derivative of the present invention can be supplied simply and in a large amount, because cyanoaquacobinamide or dicyanocobinamide is employed as the starting material.

The vitamin $B_{12}$ derivative of the above formula (I) and a pharmaceutically acceptable salt thereof may be administered individually, but if necessary or desired, can be administered orally or parenterally in a desired dosage form admixed with pharmaceutically acceptable general purpose carriers, excipients, solvents, and vehicles, etc. Oral administration agents may be in the form of tablets, pills, granules, powders, solutions, suspensions, or capsules. Parenteral administration agents may be in the form of subcutaneous and dermal ointments, creams, or gels. Intratracheal agents may be administered intratracheally by use of an appropriate spraying agent such as an aerosol.

The tablet of the composition containing the vitamin $B_{12}$ derivative of the above formula (I) of the present invention or a pharmaceutically acceptable salt thereof can be prepared by mixing an excipient such as lactose, starch, or crystalline cellulose, optionally with a binder such as carboxymethyl cellulose, methyl cellulose, and polyvinyl pyrrolidone; and/or disintegrating agent such as sodium alginate and sodium hydrogen carbonate, with the active ingredient, and molding the mixture in a conventional manner. For a preparation of solutions or suspensions, for example, glycerol esters such as tricaprylin and triacetin, and alcohols such as ethanol, may be mixed with the active ingredient, and a conventional method may be applied to the mixture. For the preparation of capsules, granules, powders or solutions may be mixed together with the active ingredient and capsule forming materials such as gelatin, etc., and a capsule forming method applied thereto.

The injections may be prepared by dissolving the active ingredient in, for example, physiological saline, ethanol, or propylene glycol, depending on the form of aqueous or nonaqueous solution agent, and adding, if necessary, preservatives and stabilizers, etc.

As the suppository, conventional dosage forms such as gelatin soft capsules containing the active ingredient may be employed.

Ointments, creams and the like may be formed in a conventional manner from the active ingredient and the required carrier.

The aerosol administration agent can be prepared by using a pharmaceutically acceptable surfactant prepared from a fatty acid having 6 to 22 carbon atoms, a fatty acid polyhydric alcohol or a cyclic anhydride thereof, a propellant such as an alkane or a fluorinated alkane having not more than 5 carbon atoms, and the active ingredient.

The concentration of the vitamin $B_{12}$ derivative of the formula (I) and a pharmaceutically acceptable salt thereof, in such a pharmaceutical preparation, is not particularly limited, but is suitably about 0.001 to 50% by weight, preferably about 0.01 to 10% by weight, in the preparation. Also, the dose is not particularly limited, but is suitably 0.01 to 500 mg/day/human, preferably 0.1 to 100 mg/day/human, generally in 1 to 4 doses per day.

EXAMPLES

The present invention is now described in more detail, with reference to Examples, which in no way limit the present invention.

Example 1

Synthesis of 2-(5,6-dimethylbenzimidazolyl)ethylcyanocobinamide phosphoric acid

In Example 1, the following processes were carried out.

1) Synthesis of 1-(2-hydroxyethyl)-5,6-dimethylbenzimidazole

A 1.46 g amount of 5,6-dimethylbenzimidazole was dissolved in 50 ml of dry N,N-dimethylformamide, 0.96 g of NaH was added to the solution, and the mixture was stirred in an ice-water bath for 30 minutes. Then to the mixture was added dropwise 5 ml of ethylene chloride, the mixture was stirred at room temperature for 15 hours, and the reaction was further carried out for 24 hours while adding 0.78 g of NaH. The reaction was stopped by an addition of 50 ml of water, and the obtained reaction mixture was washed with n-hexane, diluted with water, adjusted to a pH of 2.5 with HCl, and then applied to an ion exchange column (Dowex 50 (hydrogen ion form)). An elution was effected successively with water, 30% ethanol, and ammoniacal 30% ethanol, and the fractions eluted with ammoniacal 30% ethanol were concentrated to dryness under a reduced pressure to give crude 1-(2-hydroxy-ethyl)-5,6-dimethylbenzimidazole. The conversion to this compound from 5,6-dimethylbenzimidazole was found to be 75% by an assay according to thin layer chromatography.

Further, the crude 1-(2-hydroxyethyl)-5,6-dimethylbenzimidazole was dissolved in 50% methanol, and after a removal of insolubles, purified by reverse phase liquid chromatography and concentrated to dryness under a reduced pressure, to give purified 1-(2-hydroxyethyl)-5,6-dimethylbenzimidazole.

$^{13}C$—NMR ($CDCl_3$, $\delta$ ppm) 20.13, 20.51, 48.11, 60.43, 109.54, 119,59, 130.82, 131.83.

2) Preparation of 2-cyanoethylphosphoric acid pyridinium salt

According to the method of Tenor (J. Am. Chem. Soc., p. 159–168, 1961), 2-cyanoethylphosphoric acid pyridinium salt was prepared. Namely, 1.61 g of barium 2-cyanoethylphosphate and 10 g of an ion exchange resin (Dowex 50 (hydrogen ion form)) were suspended in water, stirred at room temperature for 30 minutes, 2 ml of pyridine was added to the supernatant, the mixture was washed with water, and the mixture then concentrated to dryness under a reduced pressure, followed by an addition of pyridine to give 1 mmol/ml of 2-cyanoethylphosphoric acid pyridinium solution.

3) Synthesis of 2-(5,6-dimethylbenzimidazolyl)ethylphosphoric acid

A 0.19 g amount of the crude 1-(2-hydroxyethyl)-5,6-dimethylbenzimidazole and 2 ml of 2-cyanoethylphosphoric acid pyridinium salt solution (1 mmol/ml) were dissolved in 20 ml of dry pyridine, and the solution was concentrated to dryness under a reduced pressure. This process was repeated twice more, and further, the dried material was thoroughly dried by a vacuum pump, dissolved in 20 ml of dry pyridine, 1.67 g of dicyclohexylcarbodiimide was added thereto, and the mixture was stored at room temperature for 2 days. After an addition of water to the product, the mixture was concentrated to dryness under a reduced pressure, followed by an addition of 40 ml of an aqueous LiOH solution (0.5 N) to carry out the reaction at 100° C. for 45 minutes. The reaction mixture was filtered to give a filtrate, which was diluted with water, adjusted to a pH of 2.5 to 3, and then the mixture was applied to an ion exchange column (Dowex 50 (hydrogen ion form)). Elution was effected successively with water and 2 N pyridine, and the fractions eluted with the latter were concentrated to dryness under a reduced pressure to give 0.27 g of crude 2-(5,6-dimethylbenzimidazolyl)ethylphosphoric acid.

4) Preparation of cyanoaquacobinamide

A 1 g amount of cyanocobalamin (vitamin $B_{12}$) was dissolved in 144 ml of water, and to the solution were added 76.8 mg of an aqueous 0.33 M $Ce(NO_3)_3$ solution and 51.2 ml of 1 N NaOH solution. Subsequently, to the mixture was added 1.77 g of KCN, and after stirring at 90° to 100° C. for one hour, the mixture was cooled to room temperature, adjusted to a pH of 8.5, and then left to stand at 4° C. overnight. The mixture was then filtered, and the filtrate desalted by phenol extraction and applied to an ion exchange column (diethylaminoethyl cellulose (acetate form)). To the fractions eluted with water was added a small amount of acetic acid, and the mixture was concentrated to dryness under a reduced pressure to give crude cyanoaquacobinamide. This was further applied to a phosphocellulose column (pH 7), eluted successively with 50% ethanol and a 50 mM NaCl solution, and the fractions eluted with the latter were desalted by phenol extraction to give 800 mg of crude cyanoaquacobinamide.

5) Synthesis of 2-(5,6-dimethylbenzimidazolyl)ethylcyanocobinamide phosphoric acid A solution of 0.27 g of crude 2-(5,6-dimethylbenzimidazolyl)ethylphosphoric acid and 0.2 g of purified cyanoaquacobinamide dissolved in 5 ml of pyridine was concentrated to dryness under a reduced pressure. This process was repeated twice more, and further, the dried product thoroughly dried by a vacuum pump, followed by addition of 15 ml of dry N,N-dimethylformamide, 10 ml of dry pyridine, and 1.5 g of dicyclohexylcarbodiimide thereto. The mixture was stirred at room temperature for 12 days, and the reaction was stopped by an addition of water and KCN. The reaction mixture was desalted by phenol extraction, then applied to a phosphocellulose column (pH 3), then the fractions passed as such were applied to an ion exchange column (diethylaminoethyl cellulose (acetate form)). Further, the fractions passed as such were purified by reverse phase high performance liquid chromatography to give 50 mg of purified 2-(5,6-dimethylbenzimidazolyl)ethylcyanocobinamide phosphoric acid as a concentrated dry product. The 2-(5,6-dimethylbenzimidazolyl)ethylcyanocobinamide phosphoric acid was confirmed by reverse phase high performance liquid chromatography and thin layer chromatography to be single. Further, it was confirmed by thin layer chromatography and reverse phase high performance liquid chromatography that 1-(2-hydroxyethyl)-5,6-dimethylbenzimidazole was obtained qualitatively and quantitatively by cerium hydrolysis of 2-(5,6-dimethylbenzimidazolyl)-ethylcyanocobinamide phosphoric acid obtained.

Example 2

Synthesis of 3-(5,6-dimethylbenzimidazolyl)propylcyanocobinamide phosphoric acid In Example 2, the following processes were carried out.

1) Synthesis of 1-(3-hydroxypropyl)-5,6-dimethylbenzimidazole

To a solution of 1.46 g of 5,6-dimethylbenzimidazole dissolved in 50 ml of dry N,N-dimethylformamide was added 0.76 g of NaH, the mixture was stirred at room temperature for 30 minutes. To the mixture was added dropwise 5 ml of 3-chloro-1-propanol, and the reaction was carried out by stirring at room temperature for 2 days, followed by an addition of water to stop the reaction. Subsequently, according to the same processes as in Example 1, crude 1-(3-hydroxypropyl)-5,6-dimethylbenzimidazole was obtained. The conversion to this compound from 5,6-dimethylbenzimidazole was found to be 90%.

Further, the crude 1-(3-hydroxypropyl)-5,6-dimethylbenzimidazole was dissolved in 50% methanol, purified by high performance liquid chromatography, and concentrated to dryness under a reduced pressure to give purified 1-(3-hydroxypropyl)-5,6-dimethylbenzimidazole.

$^{13}$C—NMR (CDCl$_3$ , δ ppm) 20.04, 20.40, 31.71, 41.16, 58.47, 109.97, 120.38, 131.21, 132.28.

$^1$H—NMR (CDCl$_3$, δ ppm) 2.0–2.2 (2H, m), 2.35 (3H, s), 2.37 (3H, s), 3.58 (2H, t, J=6.0 Hz), 4.30 (2H, t, J=7.0 Hz), 7.18 (1H, s), 7.54 (1H, s), 7.78 (1H, s).

2) Synthesis of 3-(5,6-dimethylbenzimidazolyl)propyl phosphoric acid

Using 0.2 g of the crude 1-(3-hydroxypropyl)-5,6-dimethylbenzimidazole and 2 ml of 2-cyanoethylphosphoric acid pyridinium salt solution (1 mmol/ml) as the starting substances, according to the same processes as in Example 1, 0.3 g of crude 3-(5,6-dimethylbenzimidazolyl)propylphosphoric acid was obtained.

3) Synthesis of 3-(5,6-dimethylbenzimidazolyl)propylcyanocobinamide phosphoric acid Using 0.3 g of crude 3-(5,6-dimethylbenzimidazolyl)propylphosphoric acid and 0.2 g of purified cyanocobinamide as the starting substances, and subsequently carrying out the same processes as in Example 1, 33 mg of purified 3-(5,6-dimethylbenzimidazolyl)propylcyanocobinamide phosphoric acid was obtained. The reaction time was made 3.5 days, and the confirmation of the compound as a single product was similar to that of Example 1. Further, it was confirmed by thin layer chromatography and reverse phase high performance liquid chromatography that 1-(3-hydroxypropyl)-5,6-dimethylbenzimidazole was obtained qualitatively and quantitatively by cerium hydrolysis of the 3-(5,6-dimethylbenzimidazolyl)propylcyanocobinamide phosphoric acid, and the $^{13}$C—NMR and $^1$H—NMR thereof were found to be identical with those of the 1-(3-hydroxypropyl)-5,6-dimethylbenzimidazole obtained in 1) of Example 2.

Example 3

Synthesis of 4-(5,6-dimethylbenzimidazoyl)butylcyanocobinamide phosphoric acid In Example 3, the following processes were carried out.

1) Synthesis of 1-(4-hydroxybutyl)-5,6-dimethylbenzimidazole

To a solution of 1.46 g of 5,6-dimethylbenzimidazole dissolved in 50 ml of dry N,N-dimethylformamide was added 0.9 g of NaH, the mixture was stirred at room temperature for 30 minutes, 8 ml of 4-chloro-1-butanol was added dropwise, and after stirring at room temperature for one day, 0.65 g of NaH and 2 ml of 4-chloro-1-butanol were further added to carry out the reaction for 8 days. Following the same processes as in Example 1, crude 1-(4-hydroxybutyl)-5,6-dimethylbenzimidazole was obtained. The conversion to this compound from 5,6-dimethylbenzimidazole was found to be 50%.

2) Synthesis of 4-(5,6-dimethylbenzimidazolyl)butylphosphoric acid

Using 0.2 g of the crude 1-(4-hydroxybutyl)-5,6-dimethylbenzimidazole and 2 ml of 2-cyanoethylphosphoric acid pyridinium salt solution (1 mmol/ml) as the starting substances, according to the same processes as in Example 1, 0.3 g of crude 4-(5,6-dimethylbenzimidazolyl)butylphosphoric acid was obtained.

3) Synthesis of 4-(5,6-dimethylbenzimidazolyl)butylcyanocobinamide phosphoric acid Using 0.3 g of the crude 4-(5,6-dimethylbenzimidazolyl)butylphosphoric acid and 0.2 g of purified cyanoaquacobinamide as the starting substances, according to the same processes as in Example 1, 15 mg of purified 4-(5,6-dimethylbenzimidazolyl)butylcyanocobinamide phosphoric acid was obtained. The reaction time was 6 days, and the compound was confirmed according to the same processes as in Example 1, by thin layer chromatography.

Example 4

Synthesis of 6-(5,6-dimethylbenzimidazolyl)hexylcyanocobinamide phosphoric acid In Example 4, the following operations were carried out.

1) Synthesis of 1-(6-hydroxyhexyl)-5,6-dimethylbenzimidazole

To a solution of 1.46 g of 5,6-dimethylbenzimidazole dissolved in 50 ml of dry N,N-dimethylformamide was added 0.84 g of NaH, and further, 8.2 ml of 6-chloro-1-hexanol. After the reaction was carried out by stirring the mixture at room temperature for one day, the reaction was stopped by an addition of water. Subsequently, according to the same processes as in Example 1, crude 1-(6-hydroxyhexyl)-5,6-dimethylbenzimidazole was obtained. The conversion to this compound from 5,6-dimethylbenzimidazole was found to be 95% or higher.

2) Synthesis of 6-(5,6-dimethylbenzimidazolyl)hexylphosphoric acid

Using 0.2 g of the crude 1-(6-hydroxyhexyl)-5,6-dimethylbenzimidazole and 2 ml of a 2-cyanoethylphosphoric acid pyridinium salt solution (1 mmol/ml), and subsequently following the same procedures as in Example 1, 0.35 g of crude 6-(5,6-dimethylbenzimidazolyl)hexylphosphoric acid was obtained.

3) Synthesis of 6-(5,6-dimethylbenzimidazolyl)hexylcyanocobinamide phosphoric acid Using 0.35 g of the crude 6-(5,6-dimethylbenzimidazolyl)hexylphosphoric acid and 0.2 g of purified cyanoaquacobinamide, and subsequently following the same processes as in Example 1, 20 mg of purified 6-(5,6-dimethylbenzimidazolyl)hexylcyanocobinamide phosphoric acid was obtained. The reaction time was 5 days, and this compound was confirmed according to the same processes as in Example 1, by thin layer chromatography.

Example 5

Synthesis of 3-imidazolylpropylcyanocobinamide phosphoric acid

In Example 5, the following processes were carried out.

1) Synthesis of 1-(3-hydroxypropyl)imidazole

To a solution of 1.7 g of imidazole dissolved in 125 ml of dioxane was added 17.25 g of potassium carbonate, and further, 13.8 ml of 3-chloro-1-propanol was added dropwise, followed by heating under reflux for 7.5 hours. The reaction mixture obtained was filtrated to remove potassium carbonate, the reaction stopped by an addition of water, and the pH adjusted to 2.5 before the reaction mixture was applied to an ion exchange column (Dowex 50 (hydrogen ion form)). Elution was effected successively with water, 30% ethanol, and ammonical 30% ethanol, and the fractions eluted with ammonical 30% ethanol were concentrated, the concentrate was applied to a phosphocellulose column (pH 8), and the fractions passed as such were concentrated to dryness under a reduced pressure, whereby 2.5 g of purified 1-(3-hydroxypropyl)imidazole was obtained.

$^{13}$C—NMR (D$_2$O, δ ppm) 34.86, 45.75, 60.51, 122.54, 130.05, 140.26.

2) Synthesis of 3-imidazolylpropylphosphoric acid

Using 0.13 g of the purified 1-(3-hydroxypropyl)imidazole and 2 ml of 2-cyanoethylphosphoric acid pyridinium solution (1 mmol/ml), and subsequently following the same processes as in Example 1, 0.2 g of crude 3-imidazolylpropylphosphoric acid was obtained.

3) Synthesis of 3-imidazolylpropylcyanocobinamide phosphoric acid

Using 0.2 g of the crude 3-imidazolylpropylphosphoric acid and 0.2 of purified cyanoaquacobinamide, and subsequently following the same processes as in Example 1, 20 mg of purified 3-imidazolylpropylcyanocobinamide phosphoric acid was obtained. The reaction time was 3 weeks, and the compound was confirmed by high performance liquid chromatography, $^{13}$C—NMR and $^1$H—NMR according to the same processes as in Example 2.

Example 6

Preparation of 2-(5,6-dimethylbenzimidazolyl)ethyladenosylcobinamide phosphoric acid To a solution of 10 mg of 2-(5,6-dimethylbenzimidazolyl)ethylcyanocobinamide phosphoric acid dissolved in 3 ml of water was added 100 mg of $NaBH_4$, and the mixture was sealed, left to stand for 15 minutes to effect reduction, 25 mg of 5'-iodo-5'-deoxyadenosine together with 3 ml of N,N-dimethylformamide were injected into the sealed vessel in the dark, and further left to stand under water cooling for 30 minutes. The following processes were carried out in the dark. To the reaction mixture were added water and 1 M potassium phosphate buffer (pH 5.0), and subsequently, the mixture was applied to an adsorption column (Amberlite XAD-2) and successively eluted with water and 80% ethanol. The fractions eluted with the latter were concentrated to dryness under a reduced pressure, the product dissolved in a small amount of water, and the solution applied to an ion exchange column (carboxymethyl cellulose (hydrogen ion form)) and successively eluted with water and 50 mM NaCl solution. The fractions eluted with the latter were desalted with an adsorption column (Amberlite XAD-2), further purified by an ion exchange column (phosphocellulose column (pH 6)), and concentrated to dryness under a reduced pressure to give purified 2-(5,6-dimethylbenzimidazolyl)ethyladenosylcobinamide phosphoric acid.

Example 7

Preparation of 3-(5,6-dimethylbenzimidazolyl)propyladenosylcobinamide phosphoric acid In Example 7, using 3-(5,6-dimethylbenzimidazolyl)propylcyanocobinamide phosphoric acid in place of 2-(5,6-dimethylbenzimidazolyl)ethylcyanocobinamide phosphoric acid in Example 6, 3-(5,6-dimethylbenzimidazolyl)propyladenosylcobinamide phosphoric acid was obtained according to the same procedures as in Example 6.

Example 8

Preparation of 4-(5,6-dimethylbenzimidazolyl)butyladenosylcobinamide phosphoric acid In Example 8, using 4-(5,6-dimethylbenzimidazolyl)butylcyanocobinamide phosphoric acid in place of 2-(5,6-dimethylbenzimidazolyl)ethylcyanocobinamide phosphoric acid in Example 6, 4-(5,6-dimethylbenzimidazolyl)butyladenosylcobinamide pholholic acid was obtained according to the same procedures as in Example 6.

Example 9

Preparation of 6-(5,6-dimethylbenzimidazolyl)hexyladenosylcobinamide phosphoric acid In Example 9, using 6-(5,6-dimethylbenzimidazolyl)hexylcyanocobinamide phosphoric acid in place of 2-(5,6-dimethylbenzimidazolyl)ethylcyanocobinamide phosphoric acid in Example 6, 6-(5,6-dimethylbenzimidazolyl)hexyladenosylcobinamide phosphoric acid was obtained according to the same procedures as in Example 6.

Example 10

Preparation of 3-imidazolylpropyladenosylcobinamide phosphoric acid

In Example 10, using 3-imidazolylpropylcyanocobinamide phosphoric acid in place of 2-(5,6-dimethylbenzimidazolyl)ethylcyanocobinamide phosphoric acid in Example 6, 3-imidazolylpropyladenosylcobinamide phosphoric acid was obtained according to the same procedures as in Example 6.

Example 11

Assay of coenzyme activity of vitamin $B_{12}$ derivative

The coenzyme activities of vitamin $B_{12}$ derivatives prepared in Examples 1 to 10 were assayed according to the two methods shown below.

1) Assay of coenzyme activity by using 3-methyl-2-benzothiazolinonehydrazone

The assay was carried out according to the method of Toraya et al. (J. Biol. Chem., vol. 252, p. 963–970, 1977).

As the enzyme, diol dehydrase was employed. This enzyme utilizes adenosylcobalamin, the vitamin $B_{12}$ coenzyme as the coenzyme and exhibits no activity if the vitamin $B_{12}$ coenzyme (adenosylcobalamin) is not present. Diol dehydrase was highly purified from *Klebsiella pneumoniae* ATCC 8724 according to the method of Poznanskaya (Arch. Biochem. Biophys., vol. 194, p. 379–386, 1979) and adjusted to a solution of 0.3 Unit/ml with 0.05 M potassium phosphate buffer (pH 8.0). As the substrate of this enzyme, a 1 M aqueous 1,2-propanediol solution was employed.

In an ice-water bath, 0.1 ml of the substrate solution, 0.1 ml of 0.5 M aqueous potassium chloride solution, 0.1 ml of diol dehydrase solution, and 0.6 ml of 0.05 M potassium phosphate buffer (pH 8.0) were mixed, and to the mixture were added, in the dark, 0.1 ml of 0.2 mM vitamin $B_{12}$ coenzyme (adenosylcobalamin), vitamin $B_{12}$ (cyanocobalamin) or each vitamin $B_{12}$ derivative prepared in Examples 1 to 10. After the mixture was incubated in the dark at 37° C. for 10 minutes, 1 ml of 0.1M potassium citrate buffer (pH 3.6) was added to stop the enzyme reaction, and then 0.5 ml of 0.1% aqueous 3-methyl-2-benzothianolinonehydrazone was added, followed by a continuation of the incubation at 37° C. for 15 minutes. To the mixture was added 1 ml of water, and the absorbance at 305 nm was measured by a Shimazu Double-beam Spectrophotometer Model UV-140-02 Model and the coenzyme activity ($k_{cat}$) was calculated.

2) Assay of coenzyme activity using alcohol dehydrogenase and reduced nicotinamide adenine dinucleotide The assay was carried out according to the method of Toraya et al. (Biochemistry, vol. 18, p. 417–426, 1979).

The diol dehydrase employed was diluted with 0.05 M potassium phosphate buffer (pH 8.0) to 0.15 Unit/ml, and 1M aqueous propanediol was used as the substrate solution. By using a 0.05 M potassium phosphate buffer (pH 8.0), 0.5 mg/ml of alcohol dehydrogenase and a 2 mM reduced nicotinamide adenine dinucleotide were prepared. To a mixture of 0.1 ml of the substrate solution, 0.1 ml of the alcohol dehydrogenase solution, 0.1 ml of the reduced nicotinamide adenine dinucleotide solution, and 0.5 ml of the 0.05 M potassium phosphate buffer (pH 8.0) was added 0.1 ml of the diol dehydrase solution. After the mixture was incubated at 37° C. for 5 minutes, there were added, in the dark, 0.1 ml of 0.2 mM vitamin $B_{12}$ coenzyme (adenosylcobalamin), vitamin $B_{12}$ (cyanocobalamin) or each vitamin $B_{12}$ derivative prepared in Examples 1 to 10, and the coenzyme activity ($k_{cat}$) was calculated by continuously monitoring the decrease in absorbance at 340 nm, by a Union Spectrophotometer SM-401.

The coenzyme activity ($k_{cat}$) measured according to the method 1) or 2) is shown in Table 1. The coenzyme activity is higher when the $k_{cat}$ is larger. The activity relative to the vitamin $B_{12}$ coenzyme (adenosylcobalamin) is also shown in % in Table 1. The vitamin $B_{12}$ derivatives prepared in Example 6 and Example 9 exhibited no coenzyme activity.

Example 12

Assay of Michaelis constant and (or) inhibition constant of vitamin $B_{12}$ derivative The Michaelis constant ($K_m$) was determined for the vitamin $B_{12}$ derivatives which exhibited a coenzyme activity in Example 11. Namely, in the method 1) in Example 11, the respective enzyme activities were assayed by suitably varying the concentration of the vitamin $B_{12}$ derivative, and Michaelis constant ($k_m$) was determined by the Lineweaver Burk plot. The results are shown in Table 1. The affinity (binding ability) for the enzyme is higher when the $K_m$ is smaller.

The inhibition constant ($K_i$) was determined for the vitamin $B_{12}$ derivatives which exhibited no coenzyme activity in Example 11. Namely, in the method 1) in Example 11, by adding adequately varied concentration of the vitamin $B_{12}$ coenzyme (adenosylcobalamin) to a fixed concentration of each vitamin $B_{12}$ derivative, the enzyme activity was respectively assayed and the inhibition constant ($K_i$) was determined by the Lineweaver-Burk plot. The results are shown in Table 1. The inhibitory activity is stronger when the $K_i$ is smaller.

TABLE 1

| Compound | $K_{cat}$ ($s^{-1}$) | (%) | $K_m$ ($\mu M$) | $K_i$ ($\mu M$) |
|---|---|---|---|---|
| Control Example (Vitamin $B_{12}$ coenzyme) | 337 | 100 | 0.80 | — |
| Example 6 | — | — | — | 52 |
| Example 7 | 199 | 59 | 0.82 | — |
| Example 8 | 167 | 50 | 11.2 | — |
| Example 9 | — | — | — | 38 |
| Example 10 | 3 | 0.9 | 1.1 | 1.0 |
| Vitamin $B_{12}$ | — | — | — | 24 |
| Example 1 | — | — | — | 1.9 |
| Example 2 | — | — | — | 0.9 |
| Example 3 | — | — | — | 3.0 |
| Example 4 | — | — | — | 43 |
| Example 5 | — | — | — | 3.7 |

Example 13

Growth promoting activity and growth inhibitory activity of vitamin $B_{12}$ derivative for *Escherichia coli* 215

*Escherichia coli* 215 is a vitamin $B_{12}$ requiring mutant strain, discovered by Ikeda et al., and is employed for the bioassay of vitamin $B_{12}$ (Vitamin, vol. 10, p. 268–279, 1956). That is, this microorganism cannot grow if vitamin $B_{12}$ is not present, and exhibits a growth depending on the presence of vitamin $B_{12}$.

The medium composition for *Escherichia coli* 215 used in this experiment is shown in Table 2.

TABLE 2

| | |
|---|---|
| $KH_2PO_4$ | 0.6 g |
| $K_2HPO_4$ | 1.4 g |
| Sodium citrate | 0.1 g |
| $MgSO_4$ | 0.01 g |
| $(NH_4)_2SO_4$ | 0.2 g |
| NaCl | 0.1 g |
| D-Glucose | 2.0 g |
| Water | 200 ml |

Into the medium shown in Table 2 were pipetted vitamin $B_{12}$ (cyanocobalamin) or each vitamin $B_{12}$ derivative synthesized in Examples 1 to 5 at various concentrations in the range of 0.1 to 100 ng/ml, and the mixture was steam-sterilized at 120 degrees for 5 minutes. *Escherichia coli* 215 microorganism cells previously cultured in a preculture medium with the same composition as the medium shown in Table 2 containing 1.5 μg/ml of L-methionine were harvested and washed thoroughly with physiological saline, and then inoculated into the test media, and stationarily cultured at 37° C. overnight. By measuring the turbidity of these culture broths at 660 nm using a Shimazu Double-beam Spectrophotometer Model UV-140-02, the growth degree of microorganism cells was determined. The molar concentration of vitamin $B_{12}$ (cyanocobalamin) or each vitamin $B_{12}$ derivative which gives ½ of the maximum growth was defined as the growth promoting activity ($K_{\frac{1}{2}(g)}$), and the results are shown in Table 3. The growth promoting activity is higher when the $K_{\frac{1}{2}(g)}$ is smaller. The vitamin $B_{12}$ derivatives synthesized in Examples 1 to 5 exhibited no growth promoting activity.

Also, to the medium shown in Table 2 was added vitamin $B_{12}$ (cyanocobalamin) at a concentration of 0.1 ng/ml, and in addition, each vitamin $B_{12}$ derivatives synthesized in Examples 1 to 5 were pipetted at various concentrations in the range of 1 to 80 ng/ml, and the mixture was steam-sterilized at 120° C. for 5 minutes. To these media were inoculated the microorganism cells precultured, harvested, and washed according to the same methods as described above, and after stationary cultivation at 37° C. overnight, the growth degree of the microorganism cells was determined by the turbidity (660 nm) of the culture broth. Also, the same experiment was conducted without an addition of the vitamin $B_{12}$ derivative, and the molar concentration of each vitamin $B_{12}$ derivative which gives ½ of the growth attained in its absence was defined as the growth inhibitory activity ($K_{\frac{1}{2}(i)}$). Further, from the following formula (V), $ID_{50}$ was calculated as the index of the competitive inhibition activity of the vitamin $B_{12}$ derivative:

$$ID_{50} = K_{\frac{1}{2}(i)}/C \qquad (V)$$

(wherein C represents the molar concentration of the added vitamin $B_{12}$ (cyanocobalamin)).

The results are shown in Table 3. The growth inhibitory activity is higher when the $K_{\frac{1}{2}(i)}$ is smaller, and the competitive inhibition activity is higher when the $ID_{50}$ is smaller.

TABLE 3

| Compound | $K_{\frac{1}{2}(g)}$ (nM) | $K_{\frac{1}{2}(i)}$ (nM) | $ID_{50}$ |
|---|---|---|---|
| Vitamin $B_{12}$ | 0.18 | — | — |
| Example 1 | — | 58.0 | 785 |
| Example 2 | — | 4.6 | 62 |

TABLE 3-continued

| Compound | $K_{\frac{1}{2}(g)}$ (nM) | $K_{\frac{1}{2}(i)}$ (nM) | $ID_{50}$ |
|---|---|---|---|
| Example 3 | — | 7.2 | 98 |
| Example 4 | — | 8.0 | 108 |
| Example 5 | — | 35.2 | 477 |

Example 14

Growth promoting activity and growth inhibitory activity of vitamin $B_{12}$ derivative for *Lactobacillus leichmannii* ATCC 7830

*Lactobacillus leichmannii* was found to be vitamin $B_{12}$-requiring by Skeggs et al. (J. Biol. Chem., vol. 184, p. 211–221, 1950), and the kit for $B_{12}$ assay with *Lactobacillus leichmannii* ATCC 7830 is readily available as a commercial product. That is, using the basal medium "Nissui" of Nissui Seiyaku for a vitamin $B_{12}$ assay with *leichmannii* as the medium for *Lactobacillus leichmannii* ATCC 7830, the medium was prepared following the method described in the instructions, and to the medium was pipetted vitamin $B_{12}$ (cyanocobalamin), or the vitamin $B_{12}$ derivative synthesized in Examples 1 to 5, each at various concentrations in the range of 0.1 to 100 ng/ml, followed by stream sterilization at 120° C. for 5 minutes. To these media were inoculated the microorganism cells, following a prescribed method, which were stationarily cultured at 37° C. overnight. The degree of growth of the microorganism cells was measured in the same manner as described in Example 13, to determine the growth promoting activity ($K_{\frac{1}{2}(g)}$). The results are shown in Table 4. The vitamin $B_{12}$ derivatives synthesized in Examples 2 to 4 exhibited a very weak growth promoting activity for this microorganism. The vitamin $B_{12}$ derivatives synthesized in Example 1 and Example 5 exhibited no growth promoting activity.

Also, to the above-mentioned basal medium was added vitamin $B_{12}$ (cyanocobalamin) at a concentration of 0.05 ng/ml, and in addition, the vitamin $B_{12}$ derivatives synthesized in Examples 1 to 5 each at various suitable concentrations, and the resultant mixture was steam-sterilized at 120° C. for 5 minutes. To these media were inoculated the microorganism cells, following a prescribed method, cultured stationarily at 37° C. overnight, and the degree of growth of the microorganism cells was measured in the same manner as described in Example 13. Also, the same experiment was carried out without adding the vitamin $B_{12}$ derivative, and the growth inhibitory activity ($K_{\frac{1}{2}(i)}$) and competitive inhibition activity ($ID_{50}$) were determined according to the method described in Example 13. The results are shown in Table 4.

TABLE 4

| Compound | $K_{\frac{1}{2}(g)}$ (nM) | $K_{\frac{1}{2}(i)}$ (nM) | $ID_{50}$ |
|---|---|---|---|
| Vitamin $B_{12}$ | 0.047 | — | — |
| Example 1 | — | 86 | 2330 |
| Example 2 | 1.5 | — | — |
| Example 3 | 0.5 | — | — |
| Example 4 | 10 | — | — |
| Example 5 | — | 213 | 5772 |

Example 15

In vivo growth inhibitory activity of vitamin $B_{12}$ derivative against mouse leukemia $L_{1210}$ cells

The mouse leukemia $L_{1210}$ cells employed for this experiment were grown and maintained intraperitoneally in DBA mice, taken out together with ascites and aseptically cultured as adapted for RPMI-1640 medium for animal cell culture supplemented with fetal bovine serum (5 v/v %) and ethanolamine (1.2 mg/liter), but devoid of vitamin $B_{12}$ (cyanocobalamin). Also, 100,000 units of penicillin and 100 mg of streptomycin were added as the antimicrobial agent, per liter of this medium. The $L_{1210}$ cells grown and adapted in vitro were further adapted to the above-mentioned medium containing 7.0 g/liter of bovine serum albumin in place of the fetal bovine serum, following the method of Fujii et al. (J. Biol. Chem., vol. 256, p. 10329–10334, 1981), and then used for experiment.

Figure 1:
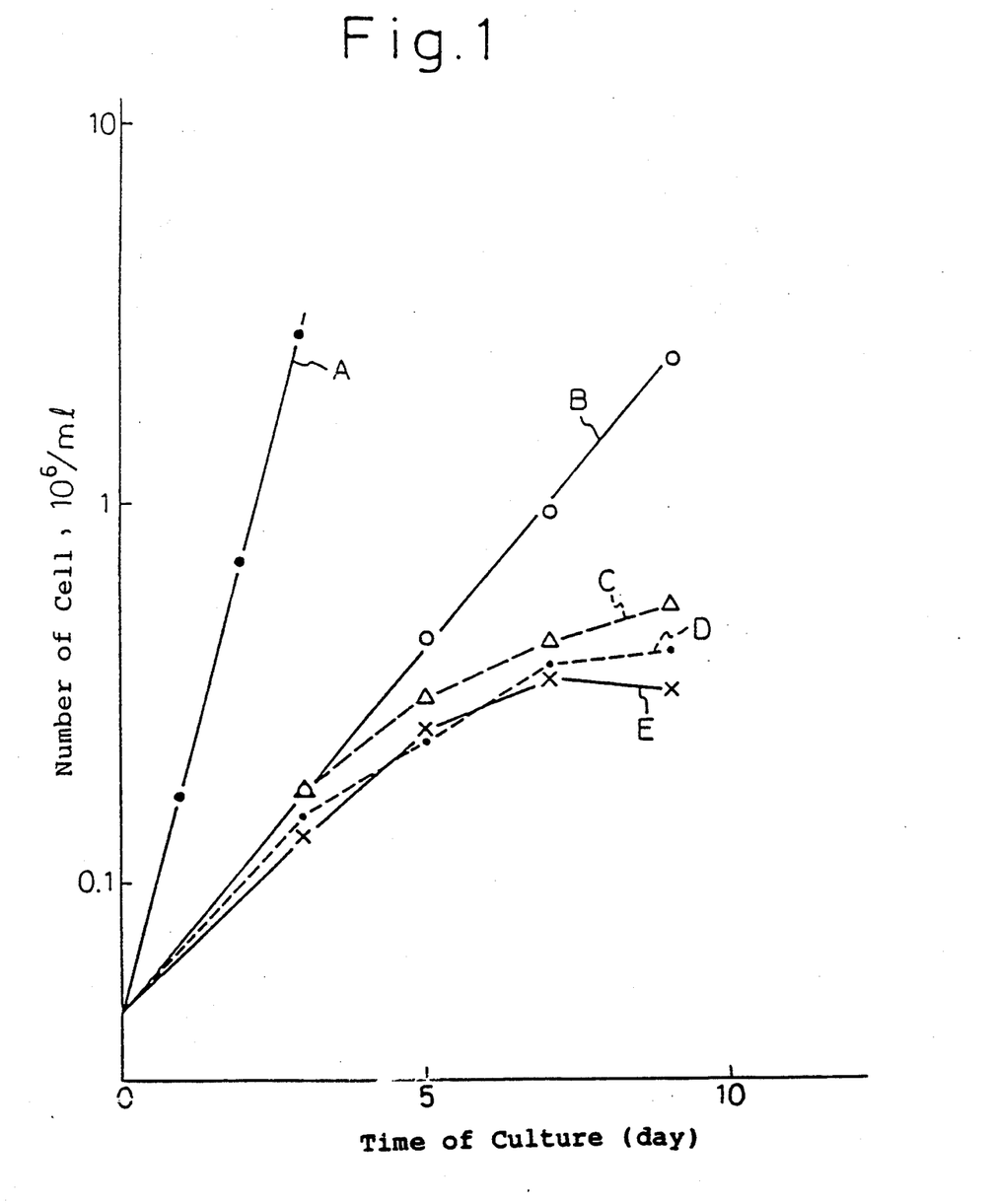
FIG. 1 shows an in vitro growth inhibitory activity of the vitamin $B_{12}$ derivative of the present invention against mouse leukemia $L_{1210}$ cells.

To examine the $L_{1210}$ growth inhibitory activities of the vitamin $B_{12}$ derivatives synthesized in Examples 2 and 5, first $L_{1210}$ cells adapted to albumin were inoculated at a density of $5 \times 10^4$ cells/ml into the same medium containing folic acid at 10 μM concentration, and a preculture was carried out under a humidified atmosphere of $CO_2$/air (5%/95%) at 37° C. for 3 days. The cells grown were centrifuged, then washed twice with the same medium containing no folic acid, to prepare an inoculum cell suspension of about $5 \times 10^6$ cells/ml. Experimental culture was carried out by adding 5-methyltetrahydrofolic acid at 10 μM and vitamin $B_{12}$ (cyanocobalamin) at 0.5 nM in place of folic acid to the above-mentioned basal medium, followed by inoculation of washed cells thereto at a density of $56 \times 10^4$ cells/ml, and continued under the above conditions for 9 days. The $L_{1210}$ cell growth inhibitory activities of the vitamin $B_{12}$ derivatives synthesized in Examples 2 and 5 were examined by permitting 200 nM of methotrexate (MTX) and each of the vitamin $B_{12}$ derivative of Example 2 (50 nM) on the vitamin $B_{12}$ derivative of Example 5 (50 nM, 5000 nM) to be co-present, respectively. The growth inhibitory activity of MTX, or a combination and of MTX and the vitamin $B_{12}$ derivative of the present invention against mouse leukemia L1210 cells was demonstrated by measurement of the cell density on days 3, 5, 7 and 9, by a Coulter counter as shown in the results in FIG. 1. As a control, the results of growth measurements when MTX and the vitamin $B_{12}$ derivative of the present invention were not added are also shown in FIG. 1. From FIG. 1, it is evident that the compound of the present invention exhibits a growth inhibitory activity against $L_{1210}$, and thus has an antitumor activity.

When the cultured cells on day 9 shown in FIG. 1 (those cultured in the presence with addition of the vitamin $B_{12}$ derivative of the present invention obtained in Example 5 (5000 nM) shown by the curve E in the Figure) was examined for their viability by staining with Trypan blue, 90% of the cells were found to be dead when both MTX and the vitamin $B_{12}$ derivative of Example 5 were co-present, while only 20% of the cells were dead when MTX above was added.

We claim:

1. A vitamin derivative, and salt thereof, represented by formula (I):

(I)

wherein L, a ligand to the cobalt of the corrin ring, is selected from the group consisting of a cyano group and an adenosyl group; B is selected from the group consisting of an imidazole group and a 5,6-dimethylbenzimidazole group; and R is a straight alkylene group having 1 to 8 carbon atoms.

2. A pharmaceutical composition comprising a vitamin derivative of claim 1, or a pharmaceutically acceptable salt thereof, as the active ingredient and a pharmaceutically acceptable excipient.

* * * * *